United States Patent [19]

Abe et al.

[11] Patent Number: 4,954,650

[45] Date of Patent: Sep. 4, 1990

[54] METHOD FOR PRODUCTION OF METHACRYLIC ACID

[75] Inventors: Tadashi Abe; Mitsuyoshi Manabe, both of Niihama; Koji Deguchi, Ibo; Hiroyuki Uhara, Tatsuno; Yukio Aoki, Ibo, all of Japan

[73] Assignees: Sumitomo Chemical Company, Ltd.; Nippon Shokubai Kagaku Kogyo Co., Ltd., both of Osaka, Japan

[21] Appl. No.: 377,119

[22] Filed: Jul. 10, 1989

[30] Foreign Application Priority Data

Jul. 11, 1988 [JP]  Japan ................... 63-172261

[51] Int. Cl.$^5$ ................ C07C 51/16; C07C 51/235; B01J 33/00; B01J 1/00; B01J 8/04; B01J 10/00; C10G 34/00

[52] U.S. Cl. ........................... 562/534; 502/2; 422/188

[58] Field of Search ........................... 562/534

[56] References Cited

U.S. PATENT DOCUMENTS 4,250,339  2/1981  Sakamoto ................ 568/471
4,487,962  12/1984  Krabetz ................ 562/534
4,816,603  3/1989  Oh-Kita ................ 562/538

FOREIGN PATENT DOCUMENTS

| 0208929 | 1/1987 | European Pat. Off. . |
| 1145602 | 3/1963 | Fed. Rep. of Germany . |
| 50-126605 | 10/1975 | Japan . |
| 56-113732 | 9/1981 | Japan . |
| 61-221149 | 10/1986 | Japan . |
| 61-291044 | 12/1986 | Japan . |
| 2603861 | 6/1981 | United Kingdom . |

*Primary Examiner*—Paul J. Killos
*Assistant Examiner*—Steven B. Jervey
*Attorney, Agent, or Firm*—Burns, Doane, Swecker & Mathis

[57] ABSTRACT

This invention relates to a improved method for the production of methacrylic acid by the steps of subjecting isobutylene and/or tertiory hutanol to catalytic vapor-phase oxidation with molecular oxygen in a first reactor, then supplying the resultant gax mixture to a second reactor, a rodlike or plate like insert set being placed in the empty space of gas inlet part of the tube of said second reactor.

9 Claims, No Drawings

4,954,650

METHOD FOR PRODUCTION OF METHACRYLIC ACID

BACKGROUND OF THE INVENTION

1. Field of the Invention

This invention relates to a method for the production of methacrylic acid by the catalytic vapor-phase oxidation of isobutylene and/or tertiary butanol. More particularly, this invention relates to a method for producing methacrylic acid from isobutylene and/or tertiary butanol by the two-step continuous reaction, namely a first step reaction which subjects isobutylene and/or tertiary butanol to catalytic vapor-phase oxidation with molecular oxygen and mainly produces methacrolein and a second step reaction which converts this methacrolein into methacrylic acid. Owing to this invention two-step continuous reaction, the trouble possibly encountered in the second step reaction, i.e. the occlusion of the catalyst bed with an occlusive substance contained in the gas formed by the first step reaction, is precluded and the production of methacrylic acid is obtained smoothly and technically stably.

2. Description of the Prior Art

In the production of methacrylic acid by the catalytic vapor-phase oxidation method from isobutylene and/or tertiary butanol, the two-step oxidation reaction is generally adopted which comprises converting isobutylene and/or tertiary butanol by the catalytic vapor-phase oxidation into methacrolein (hereinafter this reaction will be referred to as the "first step reaction" and the catalyst used therein as the "first step catalyst") and subsequently converting the methacrolein by the catalytic vapor-phase oxidation into methacrylic acid (hereinafter this reaction will be referred to as the "second step reaction" and the catalyst used therein as the "second step catalyst").

The catalyst to be used in the first step reaction is generally a multi-element type oxide catalyst containing molybdenum, bismuth, an iron. When the catalytic vapor-phase oxidation of isobutylene and/or tertiary butanol is carried out in the presence of a catalyst of this type, the reaction in addition to forming methacrolein as a main product producer by product compounds of relatively high boiling points such as maleic acid and terephthalic acid and further entails evolution of a gas containing polymers and tarry substances. When the reaction gas containing such substances is supplied in the unmodified form to the second step reaction, these substances induce clogging of the piping and occlusion of the packed bed of the second step catalyst and consequently cause aggravation of pressure loss, degradation of catalytic activity, and impairment of the selectivity of the reaction for methacrylic acid. These troubles occur frequently when the feed volume or feed rate of isobutylene and/or tertiary butanol is increased or the concentration of isobutylene and/or tertiary butanol is increased for the purpose of ensuring a large output of methacrylic acid.

Among the methods heretofore proposed and adopted for the prevention of these troubles, a method which comprises periodically discontinuing the reaction, removing from the gas inlet side of the second step catalyst an inert substance such as, for example, ceramic balls packed therein for preventing the catalyst bed from occlusion or precluding the loss of catalytic activity, and replacing a new supply of the inert substance, a method which comprise separating methacrolein from the gas produced by the first step reaction and elaborately feeding the separated methacrolein to the second step reaction thereby optimizing the process of oxidation, and a method which comprises diluting the feed gas to a concentration lower than normally required and ensuring a desired decrease in the concentration of by-products in the product of reaction are well known.

These methods, however, are invariably not close to proving satisfactory from the economic point of view because they are complicated and expensive. Further, a method which recycles as an inert gas the waste gas emanated from the reaction gas for the purpose of lowering the oxygen contents of the reaction gases formed in the first step and second step reactions to the fullest possible extent for the purpose of preventing excessive oxidation has found popular acceptance. In this connection, a method which, for the purpose of preventing the catalyst bed from occlusion and precluding the loss of catalytic activity, lowers the concentration of minute solid particles in the waste gas being recycled to the first step reaction to the fullest possible extent (Japanese Patent Laid-Open SHO 56(1981)-113,732), a method which, for the purpose of preventing the piping intervening between the sites of the first step and second step reactions from clogging, retains the portion of the piping at a temperature exceeding the boiling point of maleic anhydride or devises means for extremely increasing the linear speed of gas (Japanese Patent Laid-Open SHO 50(1975)-126,605), and a method which represses the occlusion of the second step catalyst with a solid matter from the first step reaction vessel by giving a specific form to the catalyst used in the second step reaction and consequently increasing the void ratio in the catalyst bed (Japanese Patent Laid-Open SHO 61(1986)-221,149) have been proposed. These methods also are not close to proving fully satisfactory for commercial operation.

Now that the development of the second step catalyst has advanced so much as to promise a reduction in the reaction temperature and an addition to the magnitude of load, the measure for preventing the trouble of clogging of the second step reaction vessel on the gas inlet side has been gaining all the more in significance.

An object of this invention, therefore, is to provide for the production of methacrylic acid an economically advantageous method free of the drawbacks of the prior art described above.

The inventors have found that, in the production of methacrylic acid from isobutylene and/or tertiary butanol by the catalytic vapor-phase oxidation using molecular oxygen and comprising a first-step reaction and a second step reaction, the occlusion of the second step catalyst bed with the by-products entrained by the gas produced in the first step reaction can be efficiently precluded and consequently the reaction performed on a commercial scale can be performed smoothly and stably by keeping a rodlike or platelike insert set in the reaction tube of the second step reactor on the gas inlet side thereof. This invention has been perfected as the result.

SUMMARY OF THE INVENTION

To accomplish the object described above in accordance with this invention, there is provided a method for the production of methacrylic acid, which is characterized by subjecting at least one member selected from the group consisting of isobutylene and tertiary butanol to catalytic vapor-phase oxidation with molecular oxygen in a first heat-exchanger type multitube reactor packed with an oxide catalyst containing bismuth, molybdenum, and iron thereby mainly forming methacrolein, then supplying the gas consequently formed by the reaction to a second heat-exchanger type multitube reactor connected directly to the aforementioned first reactor and packed with an oxide catalyst containing molybdenum and phosphorus thereby subjecting the methacrolein to catalytic vapor-phase oxidation with molecular oxygen and consequently forming methacrylic acid and, during the formation of methacrylic acid, keeping a rodlike or platelike insert set in the empty space of the gas inlet part of the tube of the second reactor packed with the catalyst.

The advantages of the method of this invention are that the possibility of entailing autoxidation and explosion is rare because the temperature of the gas to be introduced into the second step reaction is not required to be unduly elevated, that the catalyst which is highly active even at low temperatures can be adopted as the second step catalyst, that the empty space part is not required to be excessively elongated for the purpose of accommodating a gas-preheating layer therein, that the inevitable necessity for removing the inert carrier otherwise entailed when occlusion occurs in the inlet part of the second step catalyst bed can be obviated, and that the production of methacrylic acid can be carried out by a continuous operation under economically advantageous conditions without entailing either the occlusion with high-boiling compounds or the decline of yield even when isobutylene and/or tertiary butanol is used in a heightened concentration.

DESCRIPTION OF PREFERRED EMBODIMENT

Now, the present invention will be described more specifically hereinafter.

In the production of methacrylic acid by the catalytic vapor-phase oxidation of isobutylene and/or tertiary butanol, the two-step oxidation method is adopted frequently. This two-step oxidation method comes in two versions; a method which produces methacrylic acid by separating methacrolein from the methacrolein-containing mixed gas formed chiefly in the first step catalyst bed, supplying the separated methacrolein to the second step catalyst bed, and subjecting it to catalytic vapor-phase oxidation therein and a method which produces methacrylic acid by supplying the methacrolein-containing mixed gas directly in its unaltered form to the second step catalyst bed and subjecting it to catalytic vapor-phase oxidation therein. Optionally, either of these versions may further incorporate therein a step of recycling a combustion gas from the waste gas remaining after the recovery of useful components.

Incidentally, when the multi-element type catalyst containing bismuth, molybdenum, and iron is used as the first step catalyst, the occurrence of such high-boiling compounds as maleic acid and terephthalic acid, polymers, or tarry substances is not avoidable. Further, polymers, tarry substances, or fumy solids are thermally formed from the reaction product even within the piping. They can be formed by collision with the wall of the piping.

When the production of methacrylic acid is effected by such a process as described above, these polymers and by-product substances are inevitably circulated through the system and introduced into the reactor in a gaseous form, in the form of minute solid particles, or in a fumy form and they have strong possibility of being entrained in a large volume into the second step reactor in particular. Under these conditions, the possibility of such by-products as high-boiling compounds assuming a solid state and inducing occlusion of the inlet side of the second step catalyst bed increases in proportion as the temperature of the mixed gas introduced into the latter-step reactor decreases.

The trouble of this occlusion is liable to occur when the concentration of isobutylene and/or tertiary butanol is heightened and consequently the amount of such secondary products as high-boiling compounds and tarry substances in the gas produced by the reaction is increased. For the avoidance of the trouble of this occlusion, in addition to the methods enumerated above, an idea of elevating the temperature of the gas on the verge of entering the second step reactor or an idea of providing for the second step reactor with a preheating bed part preceding the inlet part of the catalyst bed may be conceived.

These conventional methods have problems of their own. The elevation of the temperature of the gas being supplied to the second step catalyst bed has its limit because it is subject to the restrictions imposed for the sake of curbing the autoxidation of methacrolein formed in the first step catalyst bed and avoiding entering an explosion range. When the preheating layer part for the gas is provided in the form of an empty space en route to the catalyst bed, the layer in the empty space part must be elongated to some extent and consequently the reactor must be enlarged proportionately. When the inert carrier is placed in the preheating layer part, the portion of the preheating layer part accommodating the inert carrier possibly entails the phenomenon of occlusion. The inventors have examined the troubles of occlusion caused under these conditions in search of a solution and have consequently acquired the following knowledge.

When the two-step oxidation method is adopted in the production of methacrylic acid by the catalytic vapor-phase oxidation of isobutylene and/or tertiary butanol, the gas produced by the reaction in the first step reactor is generally cooled enough for the prevention of the autoxidation and the avoidance of the explosion limit. When the temperature of the gas is lowered excessively, the by-products are converted into solids or fumy substances, which in the unaltered form are destined to induce occlusion of the second step reactor on the inlet side of the catalyst bed. For the elimination of this occlusion, the inventors have adopted a theory that the occlusion of the second step catalyst bed ought to be avoided by heightening linear speed of the gas and, in the meantime, elevating the temperature of the gas at the highest possible rate thereby enabling the by-products of the first step reaction to undergo excessive reaction readily on the second step catalyst and allowing the gas in a harmless state to pass the second step catalyst bed. After a further study on this theory, they have found that though the trouble of occlusion is not fully avoided by the packing with the inert carrier or by the preheating as in the second step catalyst bed, the preheating effect of the gas for the second step reaction is manifested, the occlusion is avoided, the reaction is continued stably for a long time, and the autoxidation of methacrolein during the course of temperature elevation can be curbed unexpectedly by simply keeping a rodlike or platelike insert set in the empty space part of the second step catalyst on the gas inlet side. This knowledge has led to perfection of this invention.

As regards the shape of the insert for use in this invention, the rodlike insert may be in the form of a straight bar, a zigzag bar, a spiral bar, a polygonal prism, or a circular column, for example, and the platelike insert in the form of a ribbon, a zigzag plate, or a spiral plate, for example. The platelike insert need not be in the form of a perfect plate but may be in the form of a reticular plate. As regards the size of the insert, the overall length is desired to be in the range of 200 to 1,000 mm, preferably 250 to 500 mm and the width is desired to be such that the void ratio may fall in the following range. The void ratio of the portion of the empty space in the gas inlet part of the second step catalyst bed is selected to suit the shape of the insert to be adopted. Generally, the void ratio is desired to be in the range of 30 to 99%. Preferably, the void ratio is in the range of 40 to 99% where the insert is in the form of a rod or in the range of 50 to 99% where the insert is in the form of a plate. By the observance of this void ratio, the occlusion of the layer of insert with solids can be precluded, the preheating effect can be attained, and the reaction in the second step catalyst bed can be performed smoothly.

The term "void ratio" as used in the present invention refers to what is defined by the following expression.

$$\text{Void Ratio (\%)} = \frac{\text{Volume of empty space} - \text{Volume of insert}}{\text{Volume of empty space}} \times 100 \, (\%)$$

The materials which are usable for the insert include metals of high thermal conductivity such as, for example, iron, nickel, aluminum, and alloys thereof. The insert made of stainless steel proves particularly desirable. The insert may be made of a metal which has undergone a chemical treatment for rust proofing the surface thereof. The ceramic insert may be obtained by forming zirconia or alumina in the shape of sheet, for example.

The present invention is desired to be worked specifically as follows. A feed gas comprising 1 to 10% by volume of isobutylene and/or tertiary butanol, 3 to 20% by volume of molecular oxygen, 0 to 60% by volume of steam, and inert gases such as nitrogen and carbon dioxide is supplied at a reaction temperature (temperature of the heat medium in the reactor) in the range of 250° to 450° C. at a space velocity in the range of 300 to 5,000 hr$^{-1}$ (STP), preferably 500 to 3000 hr$^{-1}$, to the bismuth-molybdenum-iron-containing multi-element type first step catalyst bed capable of converting isobutylene and/or tertiary butanol into methacrolein. Then, the gas produced by the first step reaction is replenished with secondary air, secondary oxygen, or steam. The resultant mixed gas is adjusted to a temperature in the range of 100° to 350° C., preferably 150° to 300° C. (namely the temperature at which no occlusion is allowed is suffered to occur within the piping and neither autoxidation nor explosion limit is suffered to ensure), and supplied to the second step catalyst having a rodlike or platelike insert set in place in the empty space of the gas inlet part thereof.

The catalyst to be used in the first step reaction is an oxide catalyst having bismuth, iron, and molybdenum as its main components. The catalyst of the following composition proves particularly desirable.

$$Mo_aW_bBi_cFe_dA_eB_fC_gD_hO_x$$

wherein Mo stands for molybenum, W for tungsten, Bi for bismuth, Fe for iron, A for at least one element selected from the group consisting of nickel and cobalt, B for at least one element selected from the group consisting of alkali metals, alkaline earth metals, and thallium, C for at least one element selected from the group consisting of phosphorus, tellurium, antimony, tin, cerium, lead, niobium, manganese, and zinc, D for at least one element selected from the group consisting of silicon, aluminum, titanium, and zirconium, and O for oxygen. Then, a, b, c, d, e, f, g, h, and x respectively stand for the numbers of atoms of the elements of Mo, W, Bi, Fe, A, B, C, D, and O such that, where a is assumed to be 12, b is in the range of 0 to 10, c in the range of 0.1 to 10, d in the range of 0.1 to 20, e in the range of 2 to 20, f in the range of 0 to 10, g in the range of 0 to 4, h in the range of 0 to 30, and x assumes a numerical value to be fixed by the states of oxidation of the elements. The oxide catalyst may be in the form of pellets produced by the use of a tableting machine or an extrusion molder, for example, in the form of beads, or in the form of rings containing a through hole. It may be effectively used in the form of a composite having a catalytic substance deposited on a refractory carrier.

The second step catalyst is only required to be an oxide catalyst containing molybdenum and phosphorus as main components. It is desired to contain a phosphomolybdic acid type heteropolyacid or a metal salt thereof. The catalyst of the following composition proves particularly desirable.

$$Mo_aP_bA_cB_dC_eD_fO_x$$

wherein Mo stands for molybdenum, P for phosphorus, A for at least on element selected from the group consisting of arsenic, antimony, germanium, bismuth, zirconium, and selenium, B for at least one element selected from the group consisting of copper, iron, chromium, nickel, manganese, cobalt, tin, silver, zinc, palladium, rhodium, and tellurium, C for at least one element selected from the group consisting of vanadium, tungsten, and niobium, D for at least one element selected from the group consisting of alkali metals, alkaline earth metals, and thallium, and O for oxygen. Then, a, b, c, d, e, f, and x respectively stand for the atomic ratio of Mo, P, A, B, C, D, and O such that, where a is assumed to be 12, b is in the range of 0.5 to 4, c in the range of 0 to 5, d in the range of 0 to 3, e in the range of 0 to 4, f in the range of 0.01 to 4, and x assumes a numerical value to be fixed by the states of oxidation of the component elements. The form in which the catalyst is used is not critical. This catalyst may be in the form of cylinders, in the form of hollow spheres, or in the form of beads. Of course, this catalyst may be used in the form of a composite having a catalytic substance deposited on a refractory carrier.

Now, the present invention will be described more specifically hereinafter with reference to working examples.

As a preliminary test, the insert specified by the present invention was tested for the effect manifested in the preheating of the gas, to obtain the following results. A steel pipe 30 mm in inside diameter and 2 mm in wall thickness was prepared, molten salt was used as a heat source, and air preheated to 255° C. was used as a feed gas. The flow volume of the air was fixed at 1.9 m3 per hour as reduced to standard conditions. When the temperature of the molten salt was fixed at 290° C., the steel pipe used in its empty form was required to have a length of about 800 to 900 mm in order to preheat the air to 280° C. When a stainless steel plate 18 mm in width corrugated with a zigzaging angle of about 90 degrees was inserted (void ratio 98%) in the steel pipe, however, the length of about 300 mm was sufficient for the pipe to preheat the air up to 280° C.

EXAMPLE 1

(Preparation of first step catalyst)

In 15 liters of water which was kept heated and stirred, 9.5 kg of ammonium molybdate and 4.9 kg were dissolved. Separately, 7.0 kg of cobalt nitrate was dissolved in 2 liters of distilled water, 2.4 kg of ferric nitrate in 2 liters of distilled water, and 2.9 kg of bismuth nitrate in 3 liters of distilled water acidified in advance by addition of 0.6 liter of concentrated nitric acid. The mixture of these three nitrate solutions was added dropwise. Then, a liquid obtained by dissolving 2.4 kg of 20% silica sol and 76 g of sodium nitrate in 1.5 liters of distilled wter was added to the mixed aqueous solution obtained as described above. The suspension consequently produced was heated and stirred for evaporation. The resultant residue of evaporation was molded and then calcined under a current of air at 450° C. for six hours, to prepare a catalyst. The metal composition of this catalyst in atomic ratio was as follows.

$Co_4Fe_1Bi_1W_3Mo_9Si_{1.35}Na_{0.1}$ (Preparation of second step catalyst)

In 40 liters of heated water, 17.7 kg of ammonium paramolybdate and 1.9 kg of ammonium metavandate were stirred and dissolved. To the resultant solution, 4 kg of pyridine and 1.25 kg of phosphoric acid (85% by weight) were added and then a mixed solution obtained by dissolving 11 kg of nitric acid. 1.8 kg of strontium nitrate, 2.5 kg of calcium nitrate, and 0.4 kg of copper nitrate in 220 liters of water was added. The resultant mixture was stirred and heated to be concentrated. The clayish substance consequently obtained was molded in a Cylindrical form of 5 mm $\phi \times$ 5 mm L ($\phi$: diameter, L: long), dried at 250° C., and calcined under a current of nitrogen at 450° C. for four hours and under a current of air at 400° C. for two hours. Consequently, there was obtained a catalyst oxide. The composition of this catalyst except for oxygen in atomic ratio was as follows.

$P_{1.3}Mo_{12}V_2Sr_{1.0}Ca_{1.5}Cu_{0.2}$ (Method of reaction)

In a reactor formed of one stainless steel reaction tube 25.4 mm in inside diameter and 5,000 mm in length and adapted to effect exchange of heat through circulation of molten salt, the aforementioned first step catalyst was packed in the form of a bed 1,700 mm in height and heated to 340° C.

In a separate reactor formed of one stainless steel reaction tube 25.0 mm in inside diameter and 5,000 mm in length and adapted to effect exchange of heat through circulation of molten salt, a stainless steel gauze was set in place at a position, 1,800 mm above the lower end of the reaction tube so as to serve as a catalyst retainer and the aforementioned second step catalyst was packed in the form of a bed 2,700 mm in height and heated to 280° C.

The two reactors thus prepared were interconnected with a conduit provided with nozzles for introduction of a molecular oxygen-containing gas and steam and further provided with a heat-exchanger, so as to permit introduction of the gas formed by the reaction in the reactor containing the first step catalyst into the reactor containing the second step catalyst. In this case, the temperature of the gas kept at 220° C. en route to the entrance to the second step reaction tube inside the second step reactor.

Further, in the upper part (the reaction gas inlet side) of the catalyst bed in the second step reaction tube, a metallic plate 300 mm in overall length formed by corrugating a stainless steel plate (SUS 304) 0.4 mm in wall thickness and 17 mm in width with a zigzag angle of about 90 degrees and a zigzag pitch of 35 mm was inserted so as to extend from the point 220 mm from the inlet part of the reaction tube to the upper end of the second step catalyst bed. In this case, the void ratio in the portion accommodating the corrugated metallic plate was 98%.

Through the gas inlet part of the first step catalyst bed, a mixed gas consisting of 4.5% by volume of isobutylene, 10.0% by volume of oxygen, 15.0% by volume of steam, and the balance of nitrogen gas was supplied to the first step catalyst at a flow rate of 1,100 N.liters per hour. Then, at the inlet to the second step catalyst bed, the feed gas was replenished with secondary air in such an amount as to adjust the molar ratio of oxygen ($O_2$) to methacrolein (MAL), $O_2$/MAL, to 2.5. At this time, the pressure difference between the inlet and outlet of the second step reactor was 160 mmHg. This reaction was continued for 2,000 hours. In this while, the temperatures of the molten salt in the first step and second step reactors were required to be elevated respectively by 3° C. and 2° C.

The results of the reaction at the outset of the reaction and after 2,000 hours' reaction were as shown in Table 1. The conversion of isobutylene shown in the table was calculated from the amount of isobutylene consumed on the way from the inlet part of the first step reactor to the outlet part of the second step reactor and the one-pass yield of methacrylic acid was expressed as the ratio of the amount of methacrylic acid formed at the outlet of the second step reactor to the amount of isobutylene supplied to the first step reactor.

Control 1

The same reactors as used in Example 1 were prepared, except that the use of the insert on the inlet side of the second step catalyst bed of the second step reactor was omitted and the second step catalyst was packed after the pattern of Example 1 so that the upper surface of the catalyst bed might rises to 500 mm from the inlet side of the reactor.

The performance of the reaction at the outset thereof was as shown in Table 1. During a protracted continuance of this reaction, the pressure difference between the outlet and inlet of the second step reactor rose to 243 mmHg after about 800 hours' reaction (Control 1—1). When the reaction was discontinued and the second step reactor was examined, it was found that the inlet side catalyst bed of the second step catalyst was occluded with polymers. To avoid this occlusion, the empty space part on the inlet side of the second step catalyst bed was given a length of 1,500 mm. The results at the outset of the reaction and after 2,000 hours reaction' were as shown in Table 1. The reaction was carried out by following the procedure of Example 1, except for the point mentioned above (Control 1-2).

It is clearly noted from Table 1 that the length of the empty space part was elongated, it induced autoxidation (evidenced increase in the amounts of carbon monoxide and acetic acid) and lead to decline of yield. In spite of the empty space, the pressure loss was increased, though slightly, after 2,000 hours' reaction.

EXAMPLE 2

A reaction was carried out by faithfully following the procedure of Example 1, except that tertiary butanol was used in place of isobutylene. The results at the outset of the reaction and after 2,000 hours' reaction were as shown in Table 1.

EXAMPLE 3

A reaction was carried out by following the procedure of Example 1, except that the temperature of the molten salt was set to 345° C. in the first step reactor and 285° C. in the second step reactor and a mixed gas consisting of 7.0% by volume of isobutylene, 14.0% by volume of oxygen, 15% by volume of steam, and the balance of nitrogen gas was supplied to the first step catalyst bed. The results at the outset of the reaction and after 2,000 hours' reaction were as shown in Table 1. It is clearly noted from Table 1 that no increase of pressure loss was recognized when the concentration of isobutylene was increased.

EXAMPLE 4

A spiraled insert having a width 23 mm and a pitch of 45 mm was prepared of a metal plate of the same material and dimensions as the metal plate used in Example 1. This insert had an overall length of 300 mm (void ratio 97.5%). The reaction was carried out by following the procedure of Example 1. The results were as shown in Table 1.

EXAMPLE 5

A reaction was carried out by following the procedure of Example 1, except that a corrugated insert having a zigzag angle of about 90 degrees and a zigzag pitch of about 35 mm and measuring 300 mm in overall length which was formed of a cylindrical metallic bar made of stailess steel (SUS 304) and possessed of an outside diameter of 5 mm was used instead. The void ratio in this case was about 96%. The reaction results were as shown in Table 1.

Control 2

A reaction was carried out by following the procedure of Example 1, except that the reaction tube of the second step reactor was packed with stainless steel Raschig rings 10 mm in diameter and 10 mm in length instead of using the insert. The packing was so made as giving a length of 200 mm to the empty space part on the inlet side of the reactor and a height of 300 mm to the layer of the Raschig ring inserts beneath the empty space part and form a bed of the second catalyst thereunder. The void ratio of the packed bed of Raschig rings was 91%. The reaction results were as shown in Table 1.

The pressure loss between the outlet and inlet of the second step reactor increased as the reaction advanced. When the reaction was discontinued after 800 hours' operation and the second step reactor was examined. it was found that the packed bed of Raschig rings was occluded rather conspicuously with solid matters such as polymers. It is noted that the state of occlusion was heavily affected by the shape of the packing in spite of the ampleness of the void ratio.

EXAMPLE 6

In the same apparatus as used in Example 5, except that the outside diameter of the cylindrical metallic bar was increased to 19 mm and the length of the insert was set to 300 mm, with the insert disposed in the empty space part. The void ratio in this case was about 43%. The reaction was carried out by following the procedure of Example 1. The results were as shown in Table 1.

After 2,000 hours' operation, the pressure loss increased to a slight extent and not to such an extent as to impede the reaction. When the reaction was discontinued and the portion of the reactor accommodating the insert was examined, it was found that polymers were deposited only slightly on the inlet side portion of the insert.

EXAMPLE 7

A reaction was carried out by faithfully following the procedure of Example 1, except that a plate of alumina measuring 0.4 mm in wall thickness, 17 mm in width, and 300 mm in length was used as an insert.

In this case, the void ratio in the portion accommodating the alumina insert was 98.3%. The method of reaction and the method of catalyst packing were similar to those of Example 1. The result were as shown in Table 1.

TABLE 1

| | Insert used in second step reaction tube | Conversion of isobutylene (tertiary butanol) (mol %) | One-pass yield of methacrylic acid (mol %) | Pressure loss in second step reactor (mmH g) |
|---|---|---|---|---|
| Example 1 | SUS plate (zig zag) | | | |
| | at the outset | 99.0 | 68.5 | 160 |
| | after 2,000 hours' operation | 98.9 | 68.7 | 158 |
| Control 1-1 | Empty space 500 mm | | | |
| | at the outset | 99.2 | 68.4 | 156 |
| | after 800 hours' operation | 99.0 | 68.5 | 243 |
| Control 1-2 | Empty space 1,500 mm | | | |
| | at the outset | 98.9 | 67.8 | 161 |
| | after 2,000 hours' operation | 99.1 | 67.6 | 167 |
| Example 2 | SUS plate (zig zag) | | | |
| | at the outset | 100 | 68.7 | 163 |
| | after 2,000 hours' operation | 100 | 68.4 | 164 |
| Example 3 | SUS plate (zig zag) | | | |
| | at the outset | 98.5 | 67.2 | 180 |

TABLE 1-continued

| | Insert used in second step reaction tube | Conversion of isobutylene (tertiary butanol) (mol %) | One-pass yield of methacrylic acid (mol %) | Pressure loss in second step reactor (mmH g) |
|---|---|---|---|---|
| Example 4 | after 2,000 hours' operation SUS plate (spiral) | 98.4 | 67.1 | 178 |
| | at the outset | 98.8 | 68.3 | 165 |
| Example 5 | after 2,000 hours' operation SUS rod (zig zag) | 98.9 | 68.3 | 167 |
| | at the outset | 99.2 | 68.4 | 158 |
| Control 2 | after 800 hours' operation Rasching ring | 99.3 | 68.7 | 160 |
| | at the outset | 99.0 | 68.1 | 168 |
| Example 6 | after 800 hours' operation SUS rod (zig zag) | 98.8 | 67.7 | 210 |
| | at the outset | 98.6 | 68.5 | 165 |
| Example 7 | after 2,000 hours' operation Alumina sheet (plate) | 98.7 | 68.2 | 182 |
| | at the outset | 98.9 | 68.4 | 162 |
| | after 2,000 hours' operation | 99.0 | 68.5 | 165 |

SUS: Stainless steel

What is claimed is:

1. In a method for the production of methacrylic acid, in which methacrylic acid is produced by subjecting at least one member selected from the group consisting of isobutylene and tertiary butanol to catalytic vapor-phase oxidation with molecular oxygen in a first heat-exchanger type multitube reactor packed with an oxide catalyst containing bismuth, molybdenum, and iron thereby mainly forming methacrolein, then supplying the gas consequently formed by said reaction to a second heat-exchanger type multitube reactor connected directly to said first reactor and packed with an oxide catalyst containing molybdenum and phosphorus thereby subjecting said methacrolein to catalytic vapor-phase oxidation with molecular oxygen and consequently forming methacrylic acid the improvement comprising keeping a rodlike or platelike insert made of metallic material or ceramic material set in the empty space of the gas inlet part of the tube of said second reactor packed with said catalyst.

2. A method according to claim 1, wherein the void ratio in the portion said empty space in the gas inlet part of the catalyst-packed tube of the second reactor is in the range of 30 to 99% by volume.

3. A method according to claim 1, wherein the overall length of said insert is in the range of 200 to 1,000 mm.

4. A method according to claim 1, wherein said metallic material is one member selected from the group consisting of iron, nickel, stainless steel, and aluminum.

5. A method according to claim 1, wherein said ceramic material is one member selected from the group consisting of zirconia and alumina.

6. A method according to claim 3, wherein said insert possesses a rodlike form the shape of which is one member selected from the group consisting of straight rod, zigzag rod, spiral rod, polygonal prism, cylinder, and circular column.

7. A method according to claim 6, wherein said shape is a zigzag rod.

8. A method according to claim 3, wherein said insert possesses a platelike form the shape of which is one member selected from the group consisting of ribbon, zigzag plate, and spiral plate.

9. A method according to claim 8, wherein said shape is one member selected from zigzag, spiral, and plate.

* * * * *